(12) United States Patent
Elmaleh

(10) Patent No.: US 9,974,672 B2
(45) Date of Patent: May 22, 2018

(54) MATERIAL STRUCTURES FOR INTRAVASCULAR DEVICE

(71) Applicant: David R Elmaleh, Newtown, MA (US)

(72) Inventor: David R Elmaleh, Newtown, MA (US)

( * ) Notice: Subject to any disclaimer, the term of this patent is extended or adjusted under 35 U.S.C. 154(b) by 691 days.

(21) Appl. No.: 14/054,543

(22) Filed: Oct. 15, 2013

(65) Prior Publication Data

US 2014/0200653 A1    Jul. 17, 2014

Related U.S. Application Data

(60) Provisional application No. 61/714,209, filed on Oct. 15, 2012.

(51) Int. Cl.
| | | |
|---|---|---|
| *A61F 2/90* | (2013.01) | |
| *A61F 2/82* | (2013.01) | |
| *A61L 31/02* | (2006.01) | |
| *A61L 31/08* | (2006.01) | |
| *A61F 2/07* | (2013.01) | |

(52) U.S. Cl.
CPC ............... *A61F 2/90* (2013.01); *A61F 2/82* (2013.01); *A61L 31/022* (2013.01); *A61L 31/088* (2013.01); *A61F 2002/072* (2013.01); *A61F 2250/0067* (2013.01)

(58) Field of Classification Search
CPC ........ A61F 2002/072; A61F 2250/0067; A61F 2/06; A61F 2/062; A61F 2/064; A61F 2/07; A61F 2002/0601; A61F 2002/065; A61F 2002/067; A61F 2002/068; A61F 2002/075; A61F 2002/077; A61F 2/82–2/93; A61L 31/022; A61L 31/088
See application file for complete search history.

(56) References Cited

U.S. PATENT DOCUMENTS

| | | |
|---|---|---|
| 5,123,917 A | 6/1992 | Lee |
| 5,201,757 A | 4/1993 | Heyn et al. |
| 5,409,495 A | 4/1995 | Osborn |

(Continued)

OTHER PUBLICATIONS

Australian Government, IP Australia, Examinees First Official Report, Australian App. No. 2007223947, dated Feb. 15, 2012, 3 pages.

(Continued)

*Primary Examiner* — Elizabeth Houston
*Assistant Examiner* — Tin Nguyen
(74) *Attorney, Agent, or Firm* — Dinsmore & Shohl LLP

(57) ABSTRACT

An intravascular device for keeping open a previously constricted site within a vessel is provided. The device includes an expandable substantially tubular body having a distal end and a proximal end. The device also includes a flexible amorphous glass coated metallic wire netting system that is circumferentially disposed about the body, and extends beyond at least one of the distal end or proximal end. The amorphous glass coated metallic wire netting system can expand along with the body to smooth tissue intrusion and minimize release of tissues debris at the site from closing the lumen of the vessel. The netting system can include a plurality of pores to permit communication between fluid flow within the vessel and the vessel wall, and at least one pharmacotherapeutic agent for the treatment or prevention of certain conditions. A method for placing the device at a site of interest is also provided.

15 Claims, 6 Drawing Sheets

(56) References Cited

U.S. PATENT DOCUMENTS

| | | | |
|---|---|---|---|
| 5,545,208 A | 8/1996 | Wolff et al. |
| 5,630,830 A | 5/1997 | Verbeek |
| 5,639,274 A | 6/1997 | Fischell et al. |
| 5,639,278 A | 6/1997 | Dereume et al. |
| 5,665,115 A | 9/1997 | Cragg |
| 5,759,186 A | 6/1998 | Bachmann et al. |
| 6,004,328 A | 12/1999 | Solar |
| 6,027,510 A | 2/2000 | Alt |
| 6,143,022 A | 11/2000 | Shull et al. |
| 6,240,616 B1 | 6/2001 | Yan |
| 6,245,100 B1 | 6/2001 | Davila et al. |
| 6,296,661 B1 | 10/2001 | Davila et al. |
| 6,306,162 B1 | 10/2001 | Patel |
| 6,315,794 B1 | 11/2001 | Richter |
| 6,436,132 B1 | 8/2002 | Patel et al. |
| 6,491,720 B1 | 12/2002 | Vallana et al. |
| 6,551,350 B1 | 4/2003 | Thornton et al. |
| 6,589,274 B2 | 7/2003 | Stiger et al. |
| 6,592,616 B1 | 7/2003 | Stack et al. |
| 6,632,240 B2 | 10/2003 | Khosravi et al. |
| 6,986,786 B1 | 1/2006 | Smith |
| 7,235,093 B2 | 6/2007 | Gregorich |
| 2001/0049554 A1 | 12/2001 | Ruiz et al. |
| 2002/0010489 A1 | 1/2002 | Grayzel et al. |
| 2002/0022875 A1 | 2/2002 | Strecker |
| 2002/0035394 A1 | 3/2002 | Fierens et al. |
| 2002/0045931 A1 | 4/2002 | Sogard et al. |
| 2002/0099435 A1 | 7/2002 | Stinson |
| 2003/0149475 A1 | 8/2003 | Hyodoh et al. |
| 2003/0171799 A1 | 9/2003 | Lee et al. |
| 2003/0181973 A1 | 9/2003 | Sahota |
| 2003/0195556 A1 | 10/2003 | Stack et al. |
| 2004/0098094 A1 | 5/2004 | Boyle et al. |
| 2004/0138731 A1 | 7/2004 | Johnson |
| 2005/0137677 A1 | 6/2005 | Rush |
| 2005/0192662 A1 | 9/2005 | Ward |
| 2005/0228473 A1 | 10/2005 | Brown |
| 2005/0256564 A1 | 11/2005 | Yang et al. |
| 2005/0267561 A1 | 12/2005 | Jones et al. |
| 2005/0288768 A1 | 12/2005 | Sowinski et al. |
| 2006/0036308 A1 | 2/2006 | Goshgarian |
| 2006/0129223 A1 | 6/2006 | Jabbour et al. |
| 2006/0178723 A1 | 8/2006 | Lentz et al. |
| 2006/0184237 A1 | 8/2006 | Weber et al. |
| 2006/0248871 A1 | 11/2006 | Johnson et al. |
| 2006/0271169 A1 | 11/2006 | Lye et al. |
| 2007/0034303 A1 | 2/2007 | Adar et al. |
| 2007/0100430 A1 | 5/2007 | Rudakov et al. |
| 2008/0234810 A1* | 9/2008 | Carlson ............... A61L 31/022 623/1.42 |
| 2008/0262598 A1 | 10/2008 | Elmaleh |
| 2009/0030510 A1 | 1/2009 | Ho |
| 2010/0057096 A1 | 3/2010 | Wolf |
| 2010/0131002 A1* | 5/2010 | Connor ............... A61B 17/1219 606/200 |

OTHER PUBLICATIONS

International Searching Authority, International Search Report and Written Opinion, PCT/US2009/067190, dated Feb. 4, 2010, 3 pages.

* cited by examiner

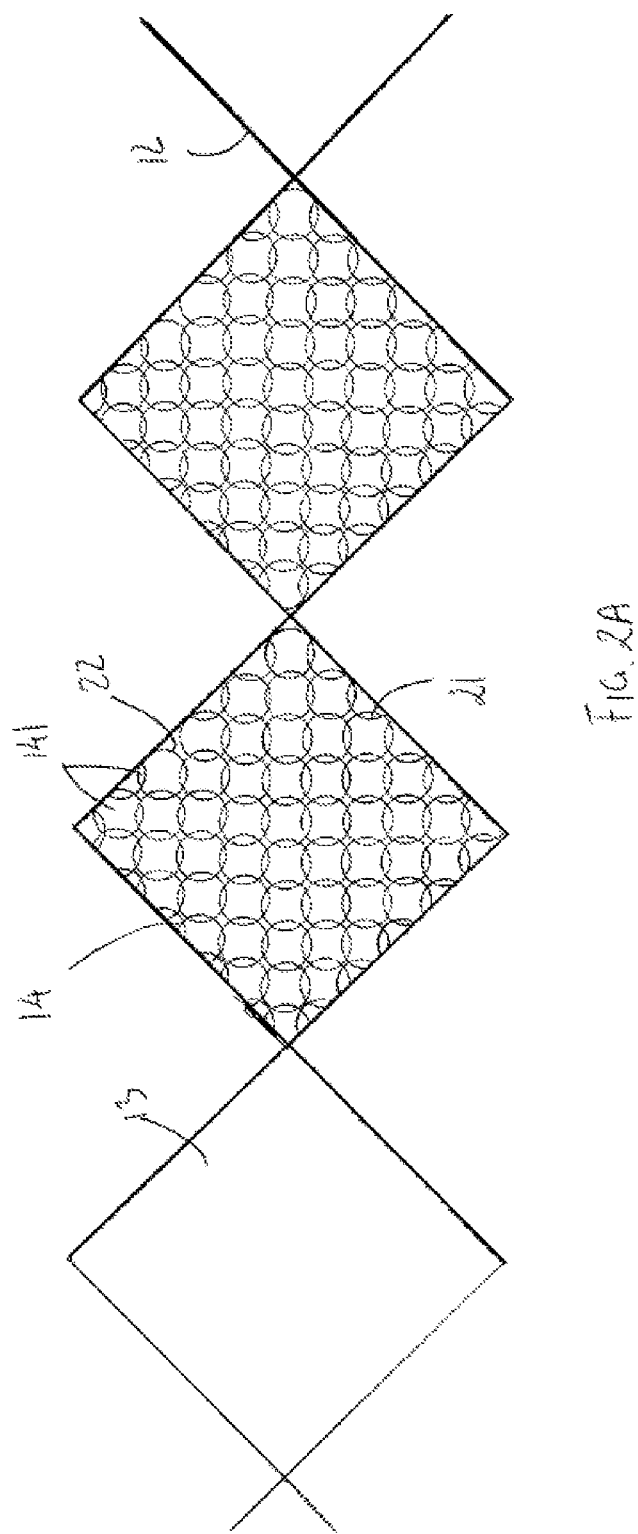

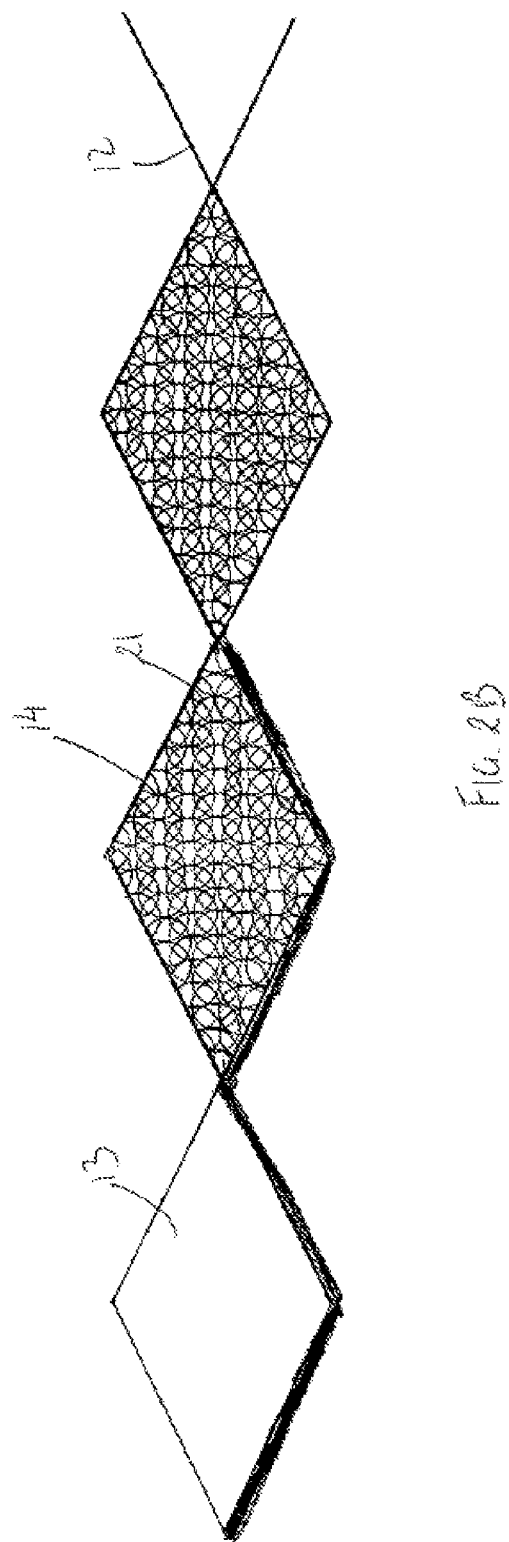

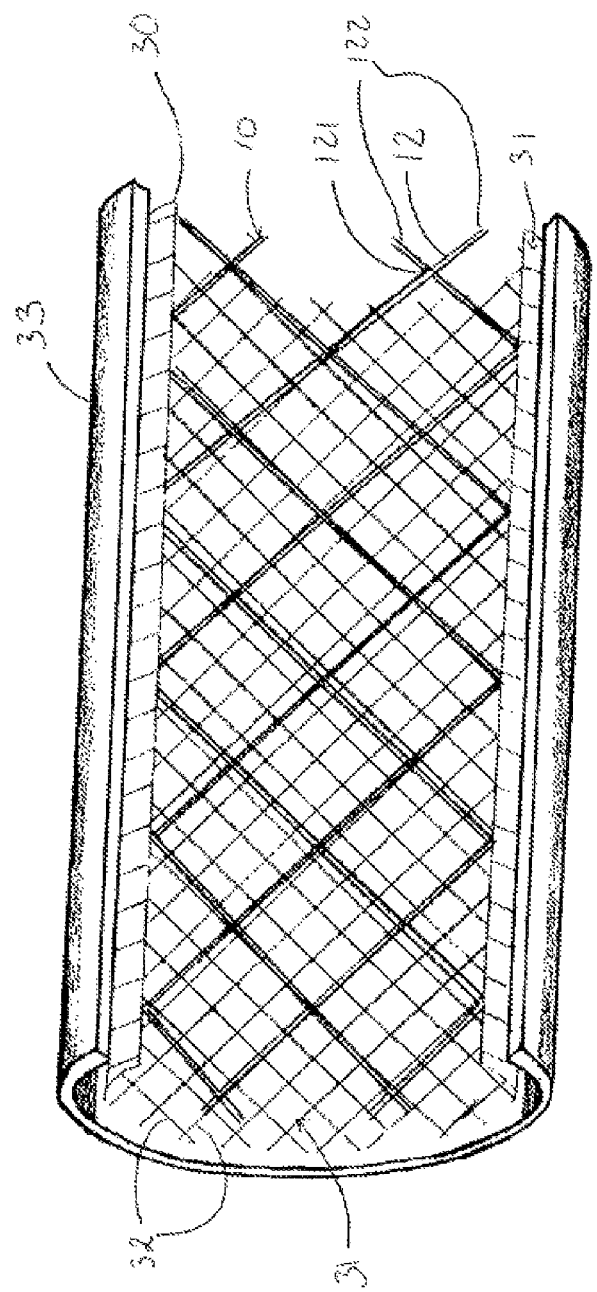

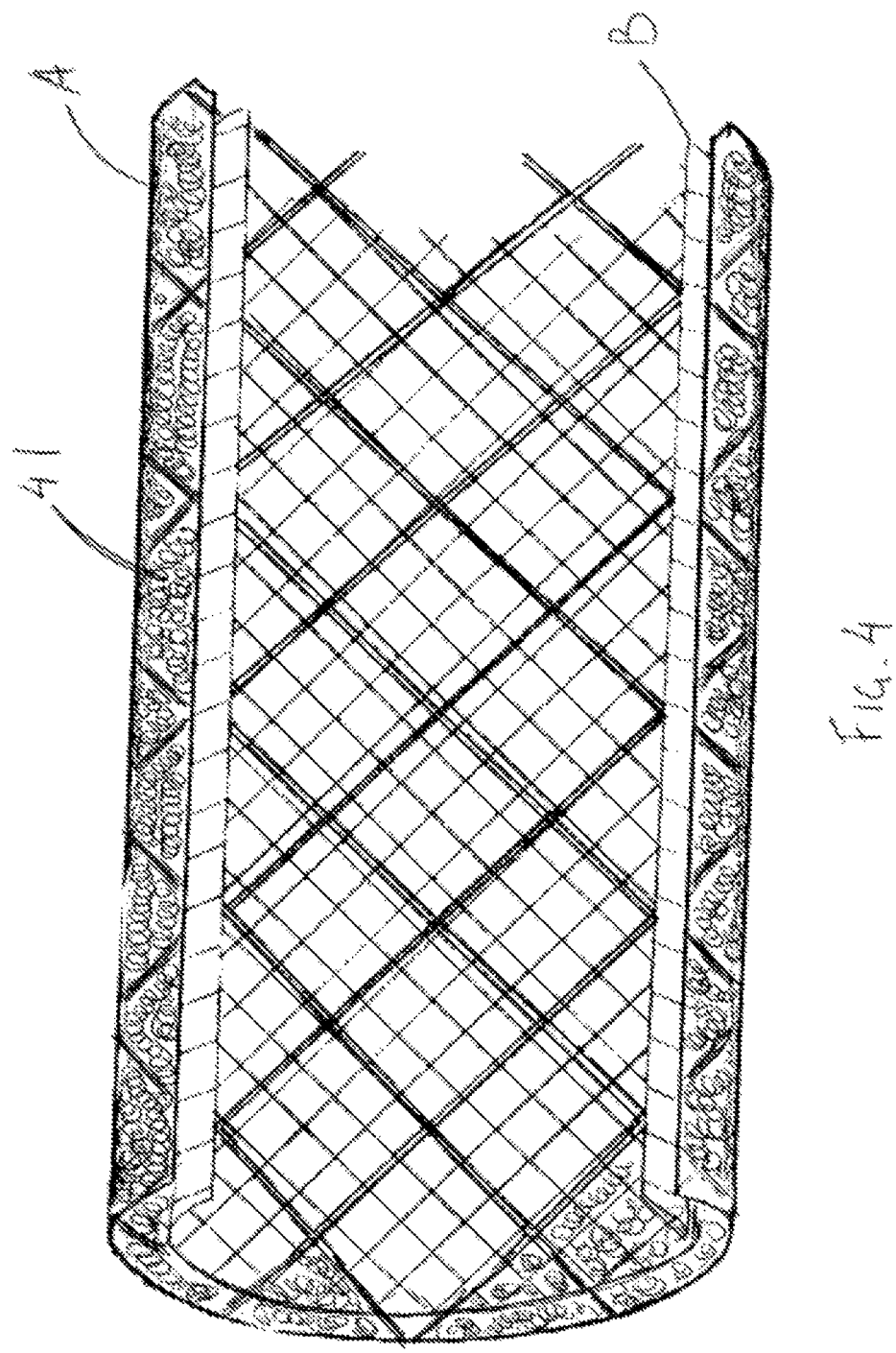

MATERIAL STRUCTURES FOR INTRAVASCULAR DEVICE

CROSS-REFERENCE TO RELATED APPLICATIONS

This application claims the benefit of U.S. provisional application No. 61/714,209 entitled "Material Structures for Intravascular Device" filed Oct. 15, 2012 by David R. Elmaleh, which is hereby incorporated by reference as though fully set forth herein.

FIELD

The present invention relates to inert intravascular devices, and more particularly, to one or more stent structural and material combination for maintaining an open lumen within a vessel for minimizing stent-tissue reactivity, lowering the inflammatory process, thrombus formation as well as release of tissue debris therefrom to prevent blockage of fluid flow within the vessel.

BACKGROUND

Many medical intravascular devices are currently being used either temporarily or permanently inside the human body to address conditions associated with cardiovascular disease, high blood pressure, diabetes, and stroke. One example of an intravascular device is a stent for use in, for instance, coronary angioplasty. Stents are small mechanical devices that can be implanted within a vascular structure, such as a blood vessel or an artery, and can be self or mechanically expanded to maintain an open lumen at a constricted location to permit a substantially clear flow path therethrough. A stent can also act to support a vessel wall in areas vulnerable to collapse. Stents can carry drug that is eluted or slowly released to treat or stabilize the vessel (DES-Drug Eluting Stents).

The mechanical reopening of a constricted vessel can sometimes lead to injuries of the tissues at the site of constriction or closure. Such injuries can often stimulate thrombus formation at such a site, as well as release of tissue debris that may subsequently act to block fluid flow within the vessel. Moreover, if permitted to proliferate, pronounced neointimal hyperplasia or restenosis can result. Furthermore, stent scaffolding cause uneven (unsmooth) vessel structure and the properties of the present metals and alloys stent structure add to the restenosis process and lower their long term efficacy. Thrombus production remains one of the most common post-stenting clinical problem, and requires effective intervention or counter-measures to prevent and/or control its reoccurrence.

Currently, methods for preventing or controlling thrombus are specifically aimed at influencing factors believed to be involved in the body's response to external or internal tissue stimulants, such as angioplasty, stenting procedures, biofilms and/or viruses. Common countermeasures which have been used to prevent or control restenosis generally fall into the one of several categories, including (1) mechanical atheroablative techniques, such as debulking, vascular filters, and emboli-trapping devices, (2) ultrasound-initiated atheroablative techniques, (3) light-assisted procedures, predominantly excimer laser angioplasty, (4) pharmacological agents and gene therapy, (5) ultraviolet photophoresis, believed to be an immune modulator, (6) radiation therapy, such as external and endovascular brachytherapy, and (7) re-stenting.

In addition, modifications to stent designs and materials have been proposed to prevent and/or control restenosis. In one approach, non-metallic, biodegradable stent materials, such as high molecular weight Poly-l-lactic acid (PLLA) is used.

Numerous inorganic coatings and surface treatments have also been developed to improve chemical inertness and biocompatibility of metallic stents. Some coatings, such as gold, however, yield a higher rate of in-stent restenosis than uncoated stents. Others, including silicon carbide and turbostatic carbon, show promise but additional studies must be done.

Organic coatings, including both synthetic and natural coatings, have also been widely studied. Among the synthetic coatings studied are Dacron, polyester, polyurethane, polytetrafluoroethylene (PTFE), polyethylacrylate/polymethylmetha-crylate, polyvinyl chloride, silicone, collagen, and iridium oxide. Results of studies, such as those with PTFE-coated stents, are disappointing or mixed at best, as there are high occurrences of late thrombo-occlusive events. With only a very few exceptions, the general consensus is that any favorable outcome was not associated with treatment of conventional in-stent restenosis using PTFE-coated stents.

Intracoronary intervention has also been employed to reduce neointima formation by reducing smooth muscle cell proliferation after balloon angioplasty. However, such intervention is often complicated by subacute and late thrombosis. Coronary thrombo-aspdrugiration and coronary pulsed-spray procedures, followed by immediate endovascular therapy, have also been particularly helpful in removing thrombotic material associated with plaque.

In addition, pharmacotherapeutic agents have been used for the treatment of some of the major post-angioplasty complications, including immunosuppresants, anticoagulants and anti-inflammatory compounds, chemotherapy agents, antibiotics, antiallergenic drugs, cell cycle inhibitors, gene therapy compounds, and ceramide therapy compounds. Pharmacotherapeutic agents can be delivered either systemically or locally. Systemic treatment has shown limited success in reducing restenosis following stent implantation, a result believed to be due to inadequate concentration of the pharmacotherapeutic agents at the site of injury. Increased dose administration, however, is constrained by possible systemic toxicity. It has been observed that local delivery of higher doses via drug eluting stents can significantly reduce adverse systemic effects. However, the local delivery of drugs via stents may be limited by the amount of surface area for drug elution.

Gene therapy has also been employed in the treatment of thrombus production. The procedure is directed towards smooth muscle cells and involves gene transfer via DNA, with or without integration of chromosomes, into selected cells. In transduction without integration, the gene is delivered to both cytoplasm and nucleus and is therefore non-selective. Gene transfer for integration employs retrovirus to affect growth stimulators.

Antibiotics, likewise, has been used in the treatment of coronary artery disease. It is known that antibiotics are effective in controlling inflammation caused by a variety of infectious agents found in fatty plaques blocking the arteries. Results of clinical investigation, such as with azithromycin, suggest a modest antibiotic benefits for heart patients.

Similarly, a phospholipid exhibiting immunosuppressive properties has been shown to block T-cell activation and proliferation, inhibit Taxol-induced cell cycle apoptosis, and activate protein kinase signal translation in malignant myogenic cells. Rapamycin and its analogs exhibit anti-tumor activities at relatively low dose levels, while inducing only mild side effects, an extremely important aspect of patient care.

SUMMARY

In one implementation, an intravascular device, such as a stent, is provided for keeping open a previously constricted intravascular site within a vessel and for minimizing stent material reactivity via an inert stent surface. In another implementation the stent structure prevents tissue debris from such a site from closing off the vessel. The device may also be used for local delivery of at least one pharmacotherapeutic agent to the intravascular site for the treatment or prevention of restenosis.

The intravascular device, in various implementations, may include a single stent structure or a plurality of structures, such as a stent disposed within another stent or a stent having an external netting system as described herein.

The intravascular device, in accordance with one implementation, includes at least one amorphous glass coated wire (e.g., an amorphous glass coated metal wire). For example, a stent constructed of amorphous glass coated metal wire is provided. In this implementation, the glass provides an inert surface and prevents platelet, macrophages and monocytes and other blood carried inflammatory enhancing molecules, tissues and viruses from precipitating and accumulating on the stent deployed vessel area.

In another implementation, the amorphous glass coated wire (e.g., an amorphous glass coated metal wire) includes an expandable substantially tubular body for placement against a vessel wall. The body of the device, in an implementation, can be defined by an amorphous glass coated metal wire framework having a plurality of small openings. In another implementation the stent can be defined by an amorphous glass coated metal wire framework having a plurality of small openings and a substructure that serves as the scaffolding for holding the vessel open. The device, defined in this implementation by an amorphous glass coated metal wire framework having a plurality of small openings, can also include a flexible amorphous glass coated metal wire netting system having a structural design for extending across each of the openings. Such a design allows the netting system to expand along with each opening in the framework to minimize occurrence of thrombus formation and tissues debris from closing the lumen of the vessel. The amorphous glass coated metal wire netting system can include a plurality of pores to permit communication between fluid flow within the vessel and the vessel wall, and at least one pharmacotherapeutic agent for the treatment or prevention of certain conditions. In one implementation, the netting system includes a plurality of amorphous glass coated metal wire extensible panels, each designed to be securely situated within an opening of the matrix. Alternatively, the netting amorphous glass coated metal wire system includes a mesh disposed on a substantially flexible matrix, such that the mesh can be placed circumferentially about the framework of the body. If desired, the amorphous glass coated metal wire flexible matrix can be provided with sufficient strength to permit the netting system to keep the lumen of the vessel temporarily open until the supporting scaffolding framework can be expanded. The device, in an implementation, can further include a second expandable substantially tubular framework concentrically positioned within the first framework of the tubular body.

If desired in another implementation the presently available bare metal, self-expendable, DES and new stents can include a second amorphous glass coated metal wire flexible netting matrix framework positioned over the first stent framework.

A method for the placement of an intravascular device within a vessel is also provided. In one implementation, the method includes initially providing a substantially tubular body defined by an amorphous glass coated wire framework (e.g., an amorphous glass coated metal wire framework) defining a plurality of openings. The substantially tubular body may be advanced along a lumen of a vessel of interest. The device may be expanded at the site of interest to allow the lumen to remain open. The device may subsequently act to elute at least one pharmacotherapeutic agent for treatment of a condition from the stent framework.

In another implementation, the method includes initially providing a device having an expandable substantially tubular body defined by an amorphous glass coated wire (e.g., an amorphous glass coated metal wire) framework having a plurality of openings, and a plurality of amorphous glass coated metal netting panels (e.g., amorphous glass coated netting panels) situated within each of the openings. Next, the device may be advanced along a lumen of the vessel to a site of interest. Thereafter, the framework may be expanded at the site of interest to allow the lumen of the vessel to remain open. The device may subsequently act to elute at least one pharmacotherapeutic agent for treatment of a condition from the first stent framework and/or from the amorphous glass coated metal wire netting panels. The netting panels may also act as a vessel surface smoothing network and to retain tissue debris between the netting panels and a vessel wall.

In yet another implementation, another method for placement of an intravascular device within a vessel is provided. In this implementation, the method includes providing a device having an expandable amorphous glass coated metal wire substantially tubular body defined by a framework having a plurality of openings, and a mesh disposed on a substantially amorphous glass coated metal wire flexible matrix loosely positioned circumferentially about the framework. Next the device may be advanced along a lumen of the vessel to a site of interest. Thereafter, the framework may be expanded at the site of interest, and the mesh on the flexible matrix be allowed to be secured between the framework and a vessel wall. In one implementation, prior to expanding the framework, the flexible matrix on which the mesh is disposed may be expanded. The device may subsequently act to elute, from the mesh, at least one pharmacotherapeutic agent for treatment of a condition. The mesh amorphous glass coated metal wire may also act to retain tissue debris between the netting panels and a vessel wall.

In another implementation, a further method for placement of an intravascular device within a vessel is provided. The method includes initially providing a device having a first expandable, substantially tubular framework including an amorphous glass coated metal wire having a plurality of openings, a plurality of amorphous glass coated metal wire netting panels situated within each of the openings, and a second expandable substantially tubular framework concentrically positioned within the first amorphous glass coated metal wire tubular framework. Next, the device may be advanced along a lumen of the vessel to a site of interest. Thereafter, the device may be expanded at the site of interest to allow the lumen of the vessel to remain open. In one implementation, the first and second tubular framework may be expanded independently. Alternatively, the first and second tubular framework may be expanded simultaneously. The device may subsequently act to elute at least one pharmacotherapeutic agent for treatment of a condition from the netting panels. The netting panels may also act to retain tissue debris between the netting panels and a vessel wall.

In another implementation, another intravascular device for maintaining an open lumen within a vessel is provided. In this implementation, the device can include an expandable substantially tubular body for placement against a vessel wall. The body can have a distal end and a proximal end. The device can also include a flexible amorphous glass coated metal wire amorphous glass coated metal wire netting system, which can be circumferentially disposed about the tubular body to reduce the occurrence of thrombus formation, and tissue debris from closing the lumen of the vessel and support a more smooth homogenous lumen wall of the vessel. The amorphous glass coated metal wire netting system can extend beyond at least one of the distal end or proximal end. The extended portion of the netting system can provide cushioning between the distal end or proximal end of the body and the vessel wall, to reduce risk of abrasion to the vessel wall by the distal end or proximal end being pushed into the vessel wall when the device is advanced and expanded in the vessel. The inert amorphous glass coated metal wire netting system can also have a smooth surface to minimize protrusion of tissue into the lumen, in order to reduce turbulence of fluid flow within the lumen of the vessel.

In another implementation, another method for placement of an intravascular device within a vessel is provided. The method includes providing a device having an expandable substantially tubular body having a distal end and a proximal end, and a flexible amorphous glass coated metal wire netting system circumferentially disposed about the tubular body, and extending beyond at least one of the distal end or proximal end following its expansion, to reduce occurrence of thrombus formation and tissue debris from closing a lumen of the vessel. Next, the device can be advanced along the lumen of the vessel to a site of interest. Thereafter, the device can be expanded at the site of interest to allow the lumen of the vessel to remain open.

In any of the implementation an amorphous glass coated metal wire could be produced from any metal, e.g., stainless steel, nickel, cobalt, cooper and/or metal alloys.

Similarly, in any of the implementations the glass coating may comprise a thickness in the range of about two microns to about four microns to provide wire flexibility and prevent the breaking of the glass coating.

BRIEF DESCRIPTION OF THE DRAWINGS

FIGS. 2A-B illustrate a detailed view of a portion of the device in FIG. 1 with an amorphous glass coated metal wire netting system in accordance with an implementation.

FIG. 3 illustrates a longitudinal section view of another amorphous glass coated metal wire intravascular device in accordance with one implementation.

FIG. 4 illustrates a perspective view of an intravascular device having concentric frameworks in accordance with another implementation.

DETAILED DESCRIPTION OF SPECIFIC IMPLEMENTATIONS

Figure 1:
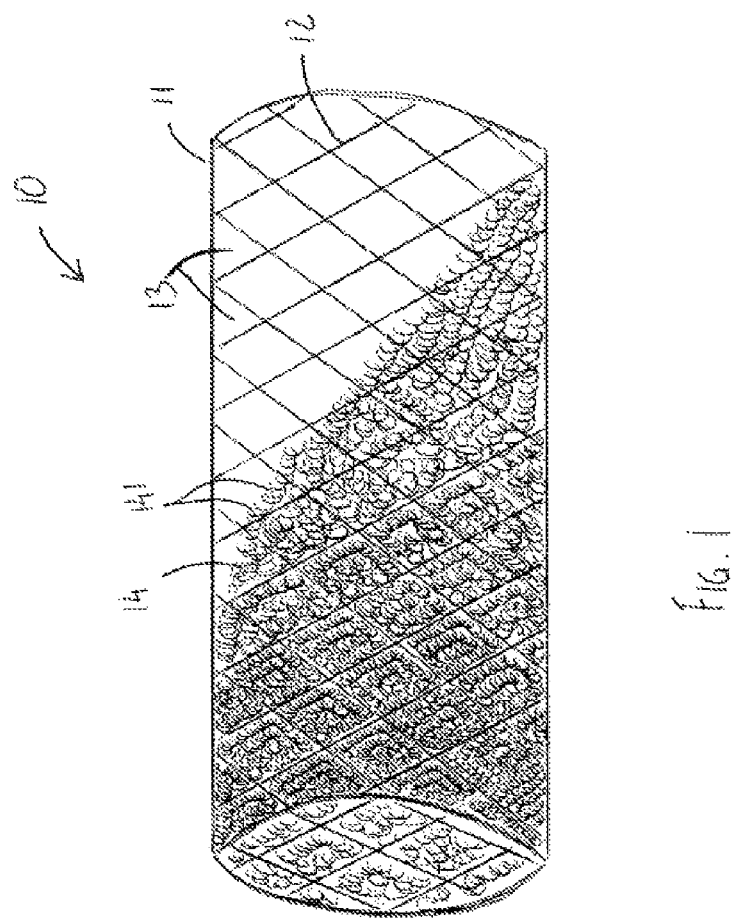
FIG. 1 illustrates a side view of an intravascular device in accordance with one implementation.

As illustrated in FIG. 1, there is shown in accordance with an implementation, an expandable intravascular device, such as a stent, for keeping open a lumen of a previously constricted intravascular site and for minimizing tissue debris from such a site from closing off the lumen. In various implementations, the stent and/or other structures include an inert amorphous glass coated metal wire. In some implementations, for example, a netting system formed by one or more amorphous glass coated metal wire provides a smooth wall vessel surface to minimize protrusion of tissue into the lumen, in order to reduce turbulence of fluid flow within the lumen of the vessel.

The device, in some implementations, may also be used for local delivery of at least one pharmacotherapeutic agent to the intravascular site for the treatment or prevention of restenosis resulting from thrombus formation.

The intravascular device 10, as illustrated in FIG. 1, includes a substantially tubular body 11 for placement against a vessel wall and structural support thereof. The body 11, in an implementation, may be defined by an expandable framework 12 having a plurality of openings 13. As the stent 10 is used to maintain an opening at a site which may have been previously constricted to provide a passage therethrough, the expandable framework 12 of stent 10 needs to be made from a biocompatible material that is sufficiently strong to maintain and support the opening. In one implementation, a material from which the framework 12 may be made includes a metal, a metal alloy, plastic, amorphous glass coated metal wire or a combination thereof. By providing the stent 10 with, for instance, an amorphous glass coated metallic wire framework 12, the stent 10 may also be visualized, for example, by fluoroscopy during placement of the stent 10 within a vessel. Of course, the framework 12 may be made from other strong materials, for instance, polymeric materials that are well known in the art.

The stent 10 may also include a flexible amorphous glass coated metallic wire netting system 14 extending across each of the openings 13 on framework 12. Since the stent 10 may be positioned at a previously constricted site, the presence of the amorphous glass coated metallic wire netting system 14 on framework 12 can act to minimize the occurrence of tissue debris at such a site from being released into the lumen of the vessel and possibly closing off the lumen. In particular, the amorphous glass coated metallic wire netting system 14 can act to retain tissue debris between it and the vessel wall. In one implementation, as the flexible amorphous glass coated metallic wire netting system 14 has elasticity, the amorphous glass coated metallic wire netting system 14 may be allowed to radially extend through openings 13 and into the lumen of the vessel at from about 0.01 mm to about 0.5 mm. Although extending into the lumen, the amorphous glass coated metallic wire netting system 14 may be designed so that such extension still permits about 75% to about 80% of the lumen to remain open for sufficient fluid flow through the vessel.

Still referring to FIG. 1, the amorphous glass coated metallic wire netting system 14 may comprise a plurality of pores 141 to permit fluid communication between a vessel wall and fluid components within the vessel, such as blood. The pores 141, in an implementation, may be disposed throughout the amorphous glass coated metallic wire netting system 14 in similar or different patterns or shapes. For example, the amorphous glass coated metallic wire netting system 14 may comprise a series of weaved or linked amorphous glass coated metallic wires 22, as shown in FIG. 2A. In one implementation, pores 141 may range from about 1/1000 to about 1/10 the size of an opening 13 in framework 12. In one particular implementation, for example, pores 141 may range from about 0.1 μm to about 100 μm. Regardless of the size, the pores 141 should act to permit fluid communication with the vessel wall while minimizing the occurrence of tissue debris from passing therethrough. In addition, it is believed that the presence of pores 141 can provide proper tissue (e.g., endothial cell) growth at, for example, a post-angioplasty stented site. Furthermore, the pores 141 may provide a space through which surrounding tissue may extend to secure the stent 10 in place.

The inert amorphous glass coated metallic wire netting system 14 may also serve as a storage and direct transport vehicle for the local delivery of, for instance, thrombus-inhibiting pharmaceuticals. To that end, the amorphous glass coated metallic wire netting system 14 may be provided with a substantially uniform thickness of a biocompatible amorphous glass coated metallic wire, so as to minimize toxic reactions from surrounding tissues. The presence of the amorphous glass coated metallic wire netting system 14 also provides additional surface area from which the pharmacotherapeutic agent can be eluted or delivered.

Examples of pharmacotherapeutic agents which may be incorporated within the framework and/or the amorphous glass coated metallic wire netting system 14 include Rapamycin, a phospholipid exhibiting immunosuppressive properties. In addition, Heparin and glycosaminoglycans are anticoagulants which may be delivered locally after intravascular device implantation. These anticoagulants interact with growth factors and other glycoproteins, which may reduce neointimal proliferation.

Abciximab is a genetically engineered fragment of a chimeric human-murine mono-clonal antibody. It is a glycoprotein inhibitor and works by inhibiting the binding of fibrinogen and other substances to glycoprotein receptor (GBIIb/IIIa) on blood platelets integral to aggregation and clotting. Abciximab appears to be effective in preventing platelet aggregation when used with aspirin and heparin, and appears to be effective in preventing abrupt closure of arteries.

Antibiotics, likewise, can be used in the treatment of coronary artery disease. It is known that antibiotics are effective in controlling inflammation caused by a variety of infectious agents found in fatty plaques blocking the arteries. Azithromycin has been observed to provide modest antibiotic benefits for heart patients.

Other pharmacotherapeutic agents which can be incorporated into the netting system 14 includes radionuclides for use in the treatment of diseased tissues, and enzymes, which may be encapsulated within a carrier, for instance, a biodegradable sol-gel capsule dispersed within the netting system 14.

It should be appreciated that the concentration of pharmacotherapeutic agent or agents, as well as the rate of release can be adjusted according to the treatment for which the stent 10 is being used, so that the release rate of the agent or agents would be appropriate and sufficient for the treatment. For example, the amorphous glass coated metallic wire netting system 14 may be coated with multiple layers, each having at least one pharmacotherapeutic agent dispersed therein.

Looking now at FIGS. 2A-B, the netting system 14 may include a plurality of individual panels 21, each securely positioned within an opening 13 of framework 12. Each of the panels 21, in an implementation, can include a structural design that provides it with sufficient strength to permit retention of tissue debris between the panel 21 and the vessel wall. In accordance with one implementation, a structural design that can be implemented includes a series of weaved or extensible chained links 22 made from, for amorphous glass coated metallic wire. Such a design also permits each panel 21 to expand along with each opening 13 during expansion of the framework 12, as shown in FIG. 2B. Of course, other structural designs may be employed, so long as they permit each panel 21 to be sufficiently strong, expand accordingly, and retain tissue debris from falling into the lumen of the vessel.

Looking now at FIG. 3, there is illustrated a netting system 30 in accordance with another implementation. An amorphous glass coated metallic wire netting system 30, as shown therein, may include a 2-4 micron glass coated metal wire mesh 31, in a form of a sheet, for example, disposed on a substantially flexible matrix 32. By providing the amorphous glass coated metallic wire netting system 30 with a flexible design, the netting system 30 may be placed circumferentially about the framework 12 of stent 10. Although flexible in design, it should be noted that the amorphous glass coated metallic wire mesh 31 and matrix 32 structurally can provide the netting system 30 with sufficient strength to retain tissue debris between the amorphous glass coated metallic wire netting system 30 and vessel wall 33. In addition, the utilization of the flexible matrix 32 can allow the amorphous glass coated metallic wire. mesh 31 thereon to expand along with the openings 13 during expansion of the framework 12. The netting system 30, in one implementation, may be loosely positioned circumferentially about the framework 12. As such, the netting system 30 may be pulled onto framework 12 or pulled off framework 12 without damaging the amorphous glass coated metallic wire netting system 30. It should be appreciated that although loosely positioned about the framework 12, subsequent to its expansion within a vessel, the netting system 30 may be pushed against the vessel wall 33 by the framework 12 to minimize movement of the amorphous glass coated metallic wire netting system 30 thereat. Alternatively, the netting system 30 may be loosely secured to various sections of framework 12, for example, at multiple intersections 121 between filaments 122. Nevertheless, similar to the non-secured implementation, the amorphous glass coated metallic wire netting system 30 may be pushed against the vessel wall 33 by the framework 12 to remain secured thereat.

In accordance with another implementation, the amorphous glass coated metallic wire netting system 30 may be provided with enhanced rigidity to permit temporary support of the vessel wall until framework 12 can be expanded. With such a design, if necessary, the netting system 30 may be expanded at the site of interest initially independently of the framework 12. Thereafter, the framework 12, concentrically positioned within the amorphous glass coated metallic wire netting system 30, may be expanded to provide the necessary support to the vessel wall. To provide the amorphous glass coated metallic wire netting system 30 with a structural design sufficient to maintain the lumen of the vessel temporarily open, the flexible matrix 32 may be designed to include from about 50% to about 70% by volume of the filaments defining the framework 12. Of course, the amount of filaments making up the flexible matrix 32 can be less, so long as the matrix can temporarily keep the vessel wall from closing until the framework 12 can be expanded. In one implementation, the strength and structural property of the amorphous glass coated metallic wire netting system 30 can be calculated or adjusted by choice of materials, amorphous glass coated nitinol, Cobalt, and other metals and metal alloys at varying size wires from 2-100 microns (preferably 2-30 microns coated with 2-4 micron glass.

As an alternate implementation, the netting system 30 may be a stent itself. In particular, looking now at FIG. 4, the netting system can be an outer stent A concentrically positioned about framework 12 (i.e., inner stent B). Although not illustrated as such, the two stents in this implementation may be substantially similar to one another (double stent). The outer stent A or the amorphous glass coated metallic wire netting system 30, in one implementation, may include individual panels 41, like the panels 21 shown in FIG. 2A, securely positioned within the openings of its framework. These panels 41, similar to panels 21, can act to retain tissue debris from falling into the lumen of the vessel, as well as to elute at least one of the pharmacotherapeutic agents noted above to a site of interest in order to minimize the occurrence of thrombus formation.

In use, intravascular device, such as stent 10 shown in FIG. 1, may be advanced along a lumen of a vessel to a site of interest, for example, a previously constricted site, an area where a cap may be thin, such as that associated with a vulnerable plaque, or a calcification site, such as that seen in carotid arteries. Thereafter, stent 10, and in particular, its framework 12, may be expanded at the site of interest to engage and support a wall of the vessel.

In the implementation where the amorphous glass coated metallic wire netting system is similar to flexible netting system 30, the framework 12 may be expanded at the site of interest, so that the amorphous glass coated metallic wire netting system 30 may be expanded along therewith. Once the framework 12 is fully expanded, the netting system 30 may be secured between the framework 12 and the vessel wall.

In an alternate implementation, where the netting system 30 may be sufficiently rigid, the netting system 30 may initially be expanded to engage the vessel wall to provide temporary support thereat. Subsequently, the framework 12, concentrically positioned within the expanded netting system 30, may be expanded to secure the netting system 30 between the vessel wall and the framework 12. A similar expansion protocol can be implemented in an implementation where the amorphous glass coated metallic wire netting system 30 may be a stent itself and a second stent exists concentrically therewithin.

Once the stent 10 has been expanded, the amorphous glass coated metallic wire netting system may be permitted to facilitate the elution of at least one pharmacotherapeutic agent to the site of interest. In addition, the amorphous glass coated metallic wire netting system may act to retain tissue debris between the netting system and a vessel wall, and allow for smoother wall environment.

Figure 5:
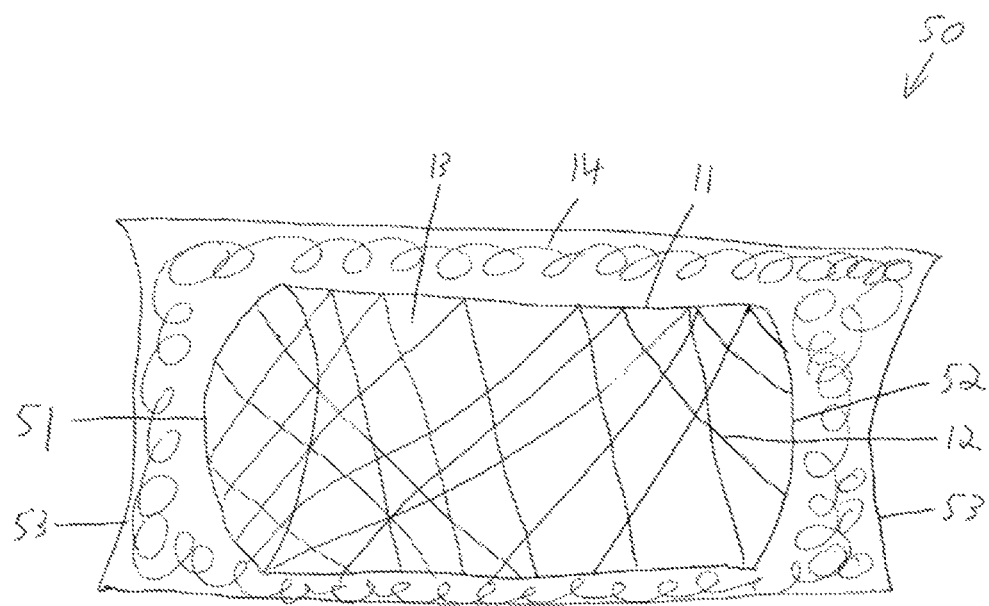
FIG. 5 illustrates an intravascular device having an amorphous glass coated metal wire netting system in accordance with an implementation.

In another implementation illustrated in FIG. 5, the flexible amorphous glass coated metallic wire netting system 14 and 30 described above, can be circumferentially disposed about the expandable tubular body 11, and can extend beyond a distal end 51 or a proximal end 52 of the tubular body 11. Alternatively, the netting system 14 can extend beyond both ends 51, 52 of the body 11. Generally, when a stent is deployed into a lumen and advanced through a vessel, there exists an inherent risk of abrasion or injury to the vessel wall. Typically, the abrasion can be caused by the edges of the rigid stent being pushed into the vessel wall during deployment. The extended portion 53 of the amorphous glass coated metallic wire netting system 14 can mitigate this risk by serving as a cushion between the distal end 51 or proximal end 52 of the body 11 and the vessel wall. The size of extension should be calculated to include the loss of length caused during the amorphous glass coated metallic wire netting system expansion. For example, if the device 10 is pushed into the vessel wall during deployment, the extended portion 53 of the flexible amorphous glass coated metallic wire netting 14 contacts the vessel wall first, and can fold or collapse onto itself to serve as a cushion between the particular body end 51 or 52 of device 10 and the vessel wall. By mitigating the risk of abrasion and injury to the vessel wall, the extended portion 53 of the netting system 14 also can reduce the occurrence of thrombus formation, and tissue debris from closing the lumen of the vessel.

Oftentimes, after deployment and expansion of a stent, the vessel wall may develop an unsmooth landscape, such as bumps and protrusions, which in turn can cause the turbulent flow of blood in the vessel and injuries that can result in thrombus formation. The flexible netting system 14 with extended portions 53 can mitigate such damage to the vessel wall by serving as a cushion between the body 11 and the vessel wall. In addition, the netting system 14 with extended portions 53 can have a smooth surface, which may act to retain tissue debris between the netting system 14 and a vessel wall. This minimizes the protrusion of tissue into the lumen, and can therefore reduce turbulence of fluid flow within the lumen of the vessel.

The flexible amorphous glass coated metallic wire is soft and its extension over the main scaffolding stent system can be from 0-100 microns longer than the end of one or both of the edges of the main scaffolding stent system.

The stent may be used to support and maintain an opening within a variety of different vessels. For instance, the stent may be placed within a coronary artery or a carotid artery to facilitate fluid flow through such arteries. By facilitating fluid flow, a heart attack or a stroke may be avoided in patients who may have calcification or vulnerable plaques within their arteries as a result of aging, high blood pressure, diabetes or other similar physical conditions. The stent may also be used to constrict a passageway, for instance, the coronary sinus, among others. To constriction a passageway, the stent may be made so that it is substantially resistant to expansion, so as to permit the tubular framework to constrict the tubular framework. The stent and/or double stent may also be used as a renal stent, gastrointestinal stent, radiation and chemotherapy stent.

While the invention has been described in connection with the specific implementations thereof, it will be understood that it is capable of further modification. For instance, the stent and/or double stent may be adapted for use with other intravascular devices for implantation within a patient's body. In addition, although in several implementations described herein multiple components of a intravascular device are constructed of an amorphous glass coated wire, other implementations may be provided in which only a subset of the components (e.g., a stent, netting) of the device may be formed by one or more amorphous glass coated wire. In a double stent implementation, for example, the outer and/or the inner stent may be formed by one or more amorphous glass coated wire while other components are formed by one or more other materials. Similarly, in a multi-component intravascular device comprising a stent and one or more other discrete netting components, the stent and/or the netting component(s) may be formed by one or more amorphous glass coated wires while other components are formed by one or more other materials. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. An intravascular device for maintaining an open lumen within a vessel, the device comprising:
   an expandable substantially tubular body for placement against a vessel wall, the expandable substantially tubular body having a distal end and a proximal end, the expandable substantially tubular body comprising at least one amorphous glass coated wire,
   wherein at least one amorphous glass coated wire defines a plurality of openings; and the device further comprises a flexible amorphous glass coated metallic wire netting system disposed within at least one of the openings, and
   wherein the netting system is secured within the at least one of the openings.

2. The intravascular device of claim 1 wherein a plurality of discrete flexible amorphous glass coated metallic wire netting systems is disposed within the plurality of openings.

3. The intravascular device of claim 1 wherein the expandable substantially tubular body is defined by a framework defining the plurality of openings.

4. The intravascular device of claim 3, wherein the framework is substantially rigid to provide structural support within the vessel.

5. The intravascular device of claim 1 wherein the at least one amorphous glass coated wire within the glass coating comprises at least one of the group comprising: Iron, Nickel, Nitinol, Cobalt, Cooper, silver, Gold, and metal alloys.

6. The intravascular device of claim 1 wherein the flexible amorphous glass coated metallic wire netting system has a structural design for extending across each of the openings, so that the flexible amorphous glass coated metallic wire netting system can expand along with each opening in the framework.

7. The intravascular device of claim 6, wherein the structural design provides the flexible amorphous glass coated metallic wire netting system with sufficient strength to permit retention of tissue debris between the flexible amorphous glass coated metallic wire netting system and the vessel wall.

8. The intravascular device of claim 1 wherein the flexible amorphous glass coated metallic wire netting system has a smooth surface to minimize protrusion of tissue into the lumen to reduce turbulence of fluid flow within the lumen of the vessel.

9. The intravascular device of claim 1 wherein the flexible amorphous glass coated metallic wire netting system includes a smooth surface to permit cushioning between the expandable substantially tubular body and the vessel wall to reduce abrasion to the vessel wall when the intravascular device is advanced and expanded in the vessel.

10. The intravascular device of claim 1 wherein the flexible amorphous glass coated metallic wire netting system includes a pharmacotherapeutic agent.

11. The intravascular device of claim 10, wherein the pharmacotherapeutic agent includes at least one of an immunosuppressant, an antibiotic, a cell cycle inhibitor, an anti-inflammatory, an anticoagulant, an antiallergenic, and a gene therapy and a ceramide therapy compound.

12. The intravascular device of claim 10, wherein the flexible amorphous glass coated metallic wire netting system provides additional surface area from which the pharmacotherapeutic agent can be eluted.

13. An intravascular device for maintaining an open lumen within a vessel, the intravascular device comprising:
    an expandable substantially tubular body for placement against a vessel wall, the expandable substantially tubular body having a distal end and a proximal end; and
    a flexible amorphous glass coated metallic wire netting system circumferentially disposed about the expandable substantially tubular body to reduce occurrence of thrombus formation and tissue debris from closing the lumen of the vessel,
    wherein the flexible amorphous glass coated metallic wire netting system is disposed within at least one of a plurality of openings defined by the expandable substantially tubular body, and
    wherein the flexible amorphous glass coated metallic wire netting system is secured within the at least one of the plurality of openings.

14. The intravascular device of claim 13 wherein the flexible amorphous glass coated metallic wire netting system has a smooth surface comprising at least one amorphous glass coated metal wire circumferentially disposed about the expandable substantially tubular body so as to minimize protrusion of tissue into the lumen to reduce turbulence of fluid flow within the lumen of the vessel.

15. The intravascular device of claim 14, wherein the flexible amorphous glass coated metallic wire netting system includes a plurality of pores therethroughout to permit communication between fluid flow within the vessel and the vessel wall.

* * * * *